| United States Patent [19] | [11] Patent Number: 4,673,641 |
| George et al. | [45] Date of Patent: Jun. 16, 1987 |

[54] CO-AGGREGATE PURIFICATION OF PROTEINS

[75] Inventors: Henry J. George, Minnetonka; Richard A. Krzyzek, Minneapolis; Lynn W. Enquist, Excelsior; Roger J. Watson, Minneapolis, all of Minn.

[73] Assignee: Molecular Genetics Research and Development Limited Partnership, Minnetonka, Minn.

[21] Appl. No.: 573,642

[22] Filed: Jan. 25, 1984

Related U.S. Application Data

[63] Continuation-in-part of Ser. No. 510,551, Jul. 6, 1983, which is a continuation-in-part of Ser. No. 436,368, Oct. 25, 1982, and a continuation-in-part of Ser. No. 400,028, Jul. 20, 1982, and a continuation-in-part of Ser. No. 450,306, Dec. 16, 1982, abandoned, and a continuation-in-part of Ser. No. 548,917, Nov. 7, 1983, abandoned.

[51] Int. Cl.$^4$ .................... C12P 21/00; C12P 21/02; C12P 21/04; C12N 15/00; C12N 1/02; C12N 1/00; C07K 3/24
[52] U.S. Cl. ........................................ 435/68; 435/70; 435/71; 435/172.3; 435/261; 435/317; 530/412; 530/418; 935/36; 935/61; 935/73
[58] Field of Search ............... 435/68, 70, 172.3, 261, 435/317, 253, 814, 820, 849, 71; 260/112 R; 935/33, 38, 60, 61; 530/412, 418, 419, 421, 810

[56] References Cited

U.S. PATENT DOCUMENTS

| 4,356,270 | 10/1982 | Itakura | 435/317 |
| 4,480,038 | 10/1984 | Cheng | 435/261 |
| 4,506,013 | 3/1985 | Hershberger et al. | 435/172.3 |
| 4,511,502 | 4/1985 | Builder et al. | 260/112 R |
| 4,511,503 | 4/1985 | Olson et al. | 260/112 R |
| 4,512,922 | 4/1985 | Jones et al. | 260/112 R |
| 4,518,526 | 5/1985 | Olson | 260/112 R |

FOREIGN PATENT DOCUMENTS

| 0072925 | 3/1983 | European Pat. Off. | 435/172.3 |
| 0080848 | 6/1983 | European Pat. Off. | 435/172.3 |
| 2007675A | 5/1979 | United Kingdom | 536/27 |

OTHER PUBLICATIONS

Itakura et al, "Expression in *Escherichia coli* of a Chemically Synthesized Gene of the Hormone Somatostatin", Science, 198: 1056 (1977).
Goedell et al., Proc. Natl. Acad. Sci. USA, 76:106-110 (1979), "Expression in *Escherichia coli* of Chemically Synthesized Genes for Human Insulin".
Williams et al., Science, 215:687-688 (1982); "Cytoplasmic Inclusion Bodies in *Escherichia coli* Producing Biosynthetic Human Insulin Proteins".
Cheng et al., Gene, 14:121-130 (1981), "Stabilization of a Degradable Protein by its Overexpression in *Escherichia coli*".
Simon et al., 1983, Proc. Natl. Acad. Sci. USA, 80:2059-2062 (1983), "Stabilization of Proteins by a Bacteriophage T4 Gene Cloned in *Escherichia coli*".
Hautala et al., Proc. Natl. Acad. Sci. USA, 76:5774-5778 (1979), "Increased Expression of a Eukaryotic Gene in *Escherichia coli* through Stabilization of its Messenger RNA".
Wetzel et al., Biochemistry, 19:6096-6104 (1980), "Production of Biologically Active Nα-desacetylthymosin α, in *Escherichia coli* through Expression of a Chemically Synthesized Gene".
Colowick and Nathan, eds., Methods in Enzymology, XXII:211-212 (1971), "Extraction of Enzymes and Protein", Academic Press, N.Y.
Hatefi and Hanstein, Proc. Natl. Acad. Sci. USA, 62:1129-1136 (1969), "Solubilization of Particulate Proteins and Non-Electrolytes by Chaotropic Agents".
Simon et al., Nature, 275: 424-428 (1978), "Bacteriophages Inhibit Degradation of Abnormal Proteins in *E. coli*."

*Primary Examiner*—James Martinell
*Attorney, Agent, or Firm*—Pennie & Edmonds

[57] ABSTRACT

Methods are provided for stabilization and purification of proteins produced in host cell systems. The methods provide for significant stabilization of any unfused nonbacterial protein that is produced in the same host cell that is producing an aggregate-forming fusion protein or any aggregate-forming protein.

14 Claims, 5 Drawing Figures

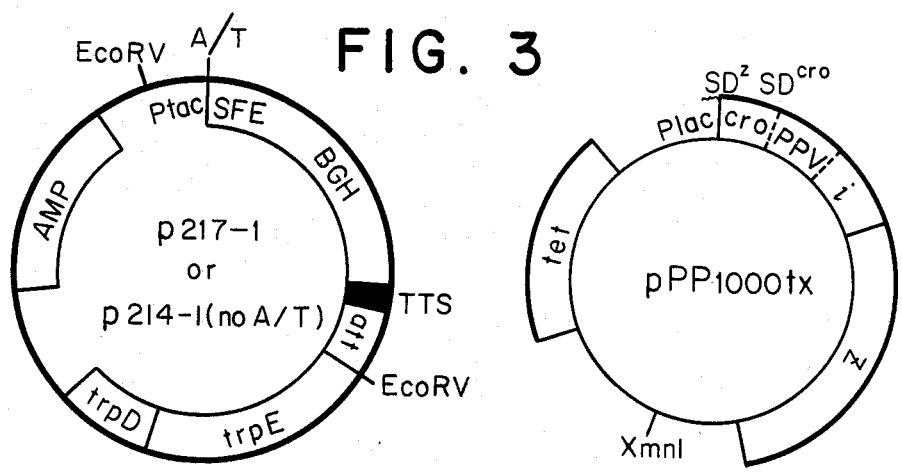
FIG. 3
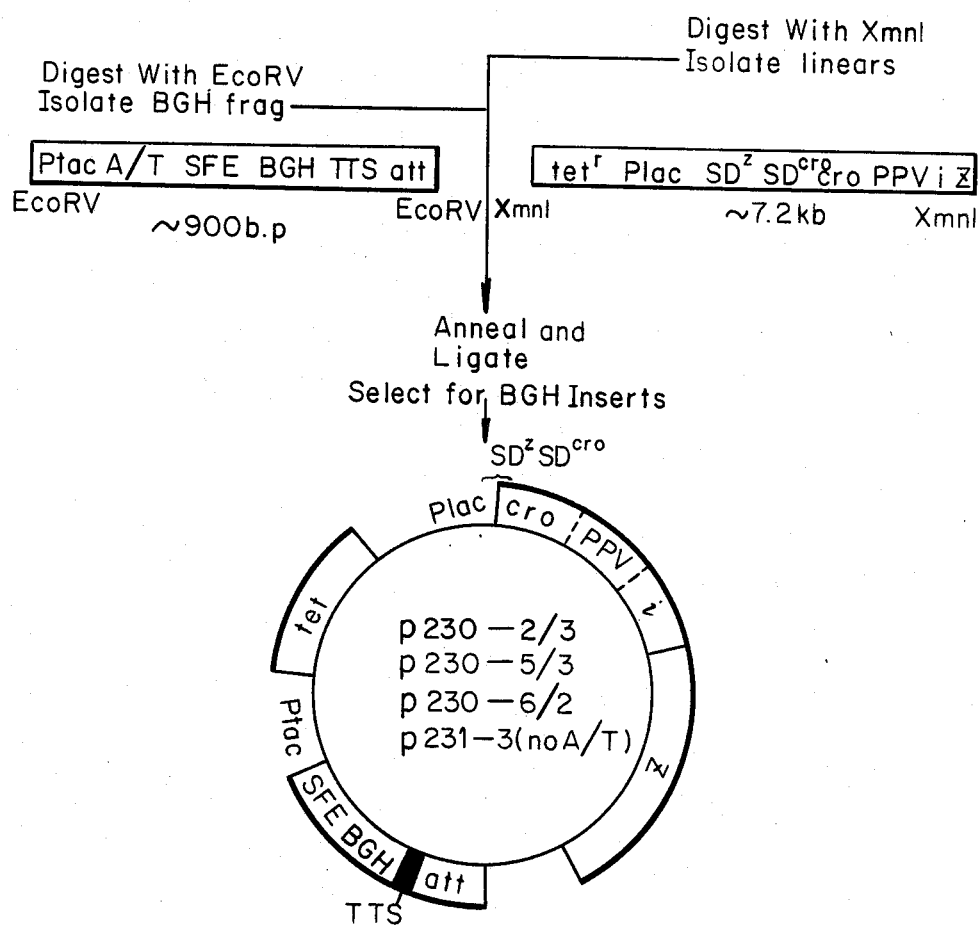

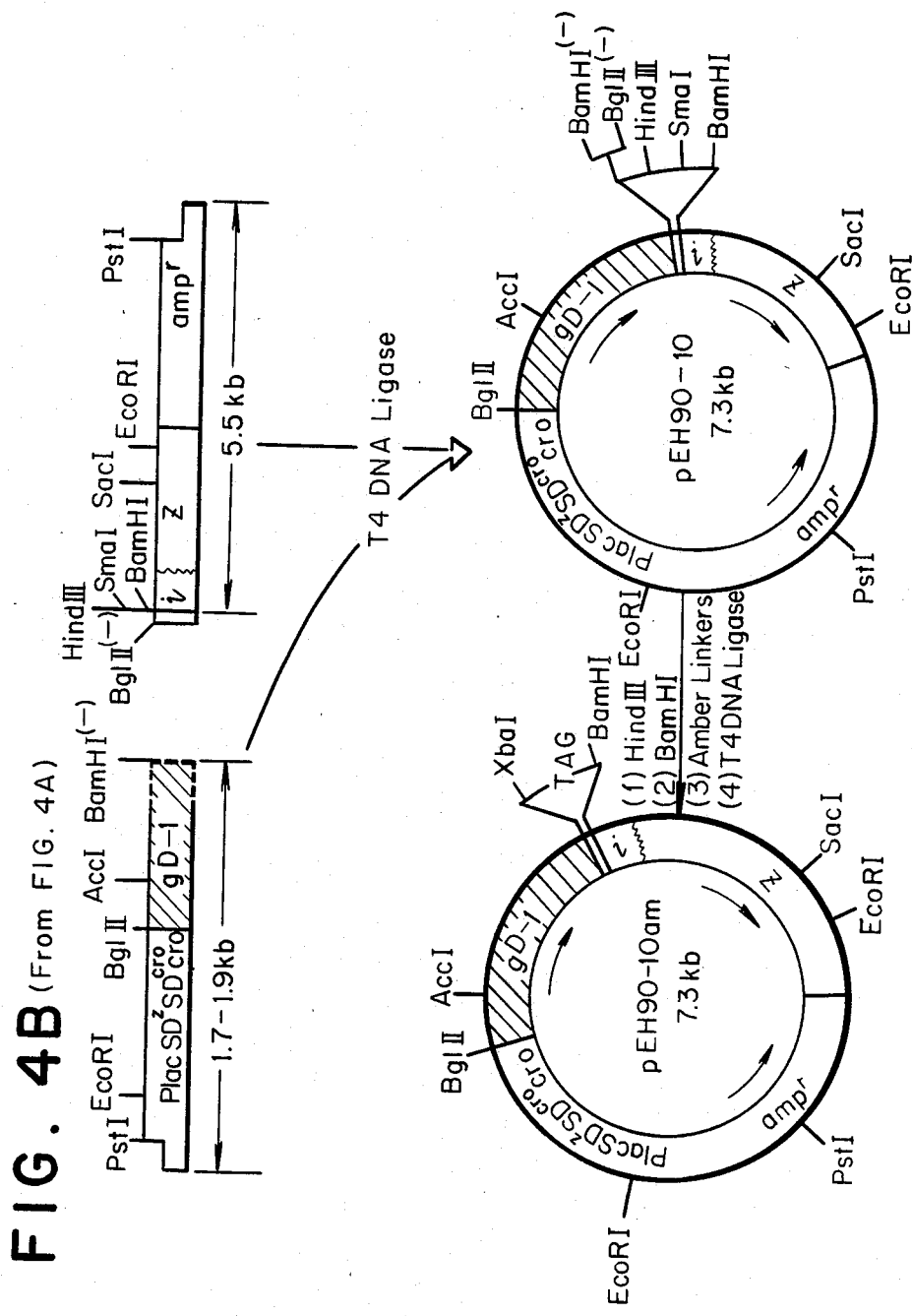
FIG. 4B (From FIG. 4A)

CO-AGGREGATE PURIFICATION OF PROTEINS

This application is a continuation-in-part of application Ser. No. 510,551, filed July 6, 1983, which in turn is a continuation-in-part of application Ser. No. 436,368, filed Oct. 25, 1982 and application Ser. No. 400,028, filed July 20, 1982. This application is also a continuation-in-part of application Ser. No. 450,306, filed Dec. 16, 1982, now abandoned. Each of such prior applications is herein incorporated by reference. This application is also a continuation-in-part of application Ser. No. 548,917, filed Nov. 7, 1983, now abandoned.

TABLE OF CONTENTS

1. FIELD OF THE INVENTION
2. BACKGROUND OF THE INVENTION
   2.1. Recombinant DNA Technology
      2.1.1. Efficient Gene Expression
   2.2. Co-Aggregation and Stabilization
3. SUMMARY OF THE INVENTION
4. BRIEF DESCRIPTION OF THE FIGURES
5. DESCRIPTION OF THE INVENTION
   5.1. Preparation of Fusion Proteins
   5.2. Preparation of Both Fused and Unfused Proteins
      5.2.1. Co-Transforamtion of Host Cells
      5.2.2. Transformation of Host Cells With One Plasmid Carrying Two Genes
      5.2.3. Modification of the Fusion Protein Gene
   5.3. Regulation of Production of Fusion Protein and Unfused Proteins
   5.4. Identification of the Gene Product
   5.5. Purification of Aggregate Forming Proteins
6. EXAMPLES
   6.1. Construction of Plasmids Which Produce Aggregate-Forming Proteins
      6.1.1. Co-Transformation With BGH Plasmid and Fusion Protein Plasmid
      6.1.2. Transforamtion of E. Coli and Expression of Fusion Proteins
      6.1.3. Stabilization of Unfused BgH Protein
      6.1.4. Insertion of BGH into PPV Fusion Protein Plasmid
      6.1.5. Analysis of Proteins Produced by Transformants
      6.1.6. Quantitation of Protein
      6.1.7. Construction of Herpes Simplex Virus Plasmids Which Produces Both Cro/gD-1 and Cro/gD-1/ β-Galactosidase Fusion Protein
7. Deposit of Microorganisms

FIELD OF THE INVENTION

The present invention relates to the stabilization and purification of proteins produced in host cell systems. Proteins that may be stabilized include eucaryotic viral, or "foreign" proteins that are labile when synthesized in bacterial cells. The term "foreign proteins" referes to any partially or synthetically made protein or one that is not normally produced by the host cell.

Many non-bacterial genes that are engineered into an apparopriate expression system in bacterial cells express non-bacterial gene products that are very susceptible to the host cell degradative enzymes. It is not surprising that these "foreign" proteins are labile when synthesized in bacterial cells since they have not evolved to exist within the bacterial cell. However, when a eucaryotic gene is properly ligated to a bacterial gene, the protein formed upon expression shows significant stabilization. These "fusion proteins" contain a portion of the bacterial protein fused to the eucaryotic protein. Fusion proteins, when produced in higher than physiologically normal amounts, tend to form insoluble aggregates either in the cell or upon cell lysis. The term "aggregate-forming protein" as used herein denotes any protein (not only fusion proteins) which forms an aggregate in aqueous solution. For example, aggregate-forming proteins produced in E. coli studied during the development of this invention include but are not limited to β-galactosidase, trpE, reverse transcriptase, bovine growth hormone, herpes simplex virus gD-fusion proteins, porcine parvovirus (PPV) fusion proteins, canine parvovirus (CPV) fusion proteins, bovine papilloma virus fusion proteins, and pseudorabies virus fusion proteins.

The present invention provides methods for the stabilization of a number of eucaryotic and viral proteins produced in bacterial cells. These methods may be used in the stabilization of any "foreign" protein that is being produced in bacterial, yeast or eucaryotic cell systems. The method of the present invention provides for significant stabilization of any unfused non-bacterial protein, such as a eucaryotic or viral protein, that is produced in the same host cell that is producing an aggregate-forming fusion protein or any aggregate-forming protein.

2. BACKGROUND OF THE INVENTION

2.1. Recombinant DNA Technology

Recombinant DNA technology involves insertion of specific DNA sequences into a DNA vehicle (vector) to form a recombinant DNA molecule which is capable of replication in a host cell. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made. In recent years several general methods have been developed which enable construction of recombinant DNA molecules. For example, U.S. Pat. No. 4,237,224 to Cohen and Boyer describes production of such recombinant plasmids using restriction enzymes and methods known as ligation. These recombinant plasmids are then introduced and replicated in unicellular organisms by means of transformation. Because of the general applicability of the techniques described therein, U.S. Pat. No. 4,237,224 is hereby incorporated by reference into the present specification.

Another method for introducing recombinant DNA molecules into unicellular organisms is described by Collins and Hohn in U.S. Pat. No. 4,304,863 which is also incorporated herein by reference. This method utilizes a packaging/transduction system with bacteriophage vectors.

Regardless of the method used for construction, the recombinant DNA molecule must be compatible with the host cell, i.e., capable of autonomous replication in the host cell. The recombinant DNA molecule should also have a marker function which allows the selection of host cells so transformed by the recombinant DNA molecule. In addition, if all of the proper replication, transcription and translation signals are correctly arranged on the plasmid, the foreign gene will be properly expressed (i.e., transcribed and translated) in the transformed cells and their progeny.

The signals and control elements for DNA replication and gene expression in eucaryotes differ from those of procaryotes. This is of critical importance when attempts are made to express in procaryotic host cells a gene which is naturally expressed only in eucaryotic cells.

These different genetic signals and processing events control many levels of gene expression, for instance, DNA transcription and messenger RNA translation. Transcription of DNA is dependent upon the presence of a promoter which is a DNA sequence that directs the binding of RNA polymerase and thereby promotes transcription. The DNA sequences of eucaryotic promoters differ from those of procaryotic promoters. Furthermore, eucaryotic promoters and accompanying genetic signals may not be recognized in or may not function in a procaryotic system.

Similarly, translation of messenger RNA (mRNA) in procaryotes depends upon the presence of the proper procaryotic signals which differ from those of eucaryotes. Efficient translation of mRNA in procaryotes requires a ribosome binding site called the Shine Dalgarno (SD) sequence on the mRNA. This sequence is a short nucleotide sequence of mRNA that is located upstream from the initiation codon (AUG) which encodes the amino-terminal methionine of the protein. The SD sequences are complementary to the 3'-end of *E. coli* 16S rRNA (ribosomal RNA) and probably promote binding of mRNA to ribosomes by duplexing with the rRNA to allow correct positioning of the ribosome. For a review on maximizing gene expression, see Roberts and Lauer, 1979, Methods in Enzymology 68: 473.

Many factors complicate the expression of eucaryotic genes in procaryotes even after the proper signals are inserted and appropriately positioned. A clear understanding of the nature of these factors and the mechanisms by which they operate is presently lacking. One such factor is the presence of an active proteolytic system in *E. coli* and other bacteria (described in Section 2.2). This protein-degrading system appears to selectively destroy "abnormal" or foreign proteins such as eucaryotic proteins. A tremendous utility, therefore, would be afforded by the development of a means to protect eucaryotic proteins produced in bacteria from proteolytic degradation.

Successful expression of a cloned gene requires efficient transcription of DNA, translation of the mRNA and in some instances post-translational modification of the protein. Expression vectors have been used to express genes in a suitable host and to increase protein production. The cloned gene should be placed next to a strong promoter which is controllable so that transcription can be turned on when necessary. Cells can be grown to a high density and then the promoter can be induced to increase the number of transcripts. These, if efficiently translated will result in high yields of protein production. This is an especially efficient system if the foreign protein is deleterious to the host cell.

2.1.1 Efficient Gene Expression

Recent studies of the major outer membrane proteins of *E. coli* which are present in large quantities in the cell have revealed some of the elements which may be responsible for high levels of gene expression. The lipoprotein (lpp) gene of *E. coli* for example, is expressed at levels reaching 700,000 to 750,000 molecules/cell, demonstrating an extremely efficient transcriptional and translational system. Other outer membrane proteins (Omp), such as those encoded by the OmpA gene and the OmpF gene are each produced in similar quantities indicating that these systems also have very efficient machinery for gene expression.

Although the mechanisms which are responsible for the highly efficient expression of these *E. coli* genes are not yet fully understood, it is believed that several factors must contribute to the abundance of such proteins in the host cell.

It has been found that in comparison with other known promoter regions of *E. coli* genes, that the promoter regions of the outer membrane protein genes are extremely A/T rich which is believed to be essential for efficient transcription of the genes. These Omp gene sequences also have regions which strongly bind RNA polymerase and are important for the initiation and efficiency of transcription of these genes.

Further analysis has revealed that A/T rich sequences are found between the SD sequence and the ATG of the Omp genes. This region (A/U on the mRNA transcript) is thought to play an important role in the initiation of translation. The A/U richness of this segment in the mRNA transcript may be needed to destabilize the secondary structure of the mRNA within this region and thereby facilitate ribosome binding and subsequent translation along the message.

Nucleotide sequence information of highly expressed genes in *E. coli* and yeast, has also shown a preferred codon "bias" which correlates well with the intracellular amounts of tRNA's for those preferred codons (i.e., a high frequency of codon usage for a particular amino acid correlates with large intracellular pools of tRNA for that amino acid). Being the most highly expressed genes in bacteria, the Omp sequences show an extreme bias for certain codons for most of the amino acids, thereby providing another factor for the highly efficient expression of these proteins within the bacterial cell.

Resolution of the DNA sequence at the 3'-end of the coding region of the Omp genes, has also disclosed a consensus-type bacterial transcription termination signal. The DNA immediately preceeding the site of transcription termination is GC-rich and possesses dyad symmetry. The 3'- terminus of the transcript typically contains a series of uridine residues. These factors contribute to the overall efficiency of transcription by hastening the rate of the mRNA production and by limiting the overall size of the mRNA transcribed from the DNA.

Finally, the presence of all three translational stop codons in the 3'- untranslated region of the mRNA transcript, all three of which are in the same translational reading frame as the "coding" frame of the mRNA, provide a sequence of tandem terminators of translation. This factor may contribute to the overall efficiency of translation by assuring proper translational termination with little chance of read-through into the untranslated region of the mRNA.

2.2 Co-Aggregation and Stabilization

Recombinant DNA techniques have been used to obtain expression of a number of foreign genes in host cells. However, difficulties in obtaining expected levels of expression have been encountered even after the proper signals are inserted and the gene is appropriately expressed. This is thought to be due to instability of the gene and its vector in the host cell, transcription inefficiencies of the cloned gene, and inefficiency of translation of the mRNA into the desired protein product. A clear understanding of the nature of these factors and the mechanisms by which they operate is presently lacking.

In some instances the cloned gene may be stable within the host cell, and it may be transcribed and translated at efficient levels, yet the gene product or protein is detected in levels significantly lower than expected. A variety of proteins, including a precursor of somatostatin and human fibroblast pre-interferon, encoded by eucaryotic genes cloned into bacterial hosts, appear to be very labile, possibly due to the degradation of these proteins by host cell proteases.

Most intact, native proteins in E. coli are very stable. However, abnormal proteins such as puromycyl polypeptide fragments and nonsense fragments of proteins are much more labile than are intact, native proteins. Although the proteins which are being encoded by eucaryotic genes are not abnormal, they may still be recognized as foreign to the bacterium, and may in turn be degraded by the host cell degradation enzyme system. The mechanisms by which foreign proteins are recognized in host cells are not well understood. However, it is critical that such degradation be minimized so that these proteins can be produced in large quantities by genetically engineered host cells.

One strategy is to construct hybrid genes in which the eucaryotic sequence is ligated in phase (i.e., in the correct translational reading frame) with a procaryotic gene such that the two gene sequences are uninterrupted by chain termination sequences. Expression of the hybrid gene by host cell transformants results in a fusion protein product (a protein that is a hybrid of procaryotic and foreign or eucaryotic amino acid sequences). An additional advantage is obtained if the host cell protein inherently contains an assayable function. The expression of the hybrid genes results in a fusion protein product that can be identified on the basis of its larger molecular weight and assayable function. For example, production of any protein fused to $\beta$-galactosidase fusion protein offers several advantages for cloning and expression of the protein in an E. coli host. First, this allows for an approximation of the level of protein production (hence expression) directed by the vector using a colorimetric assay specific for B-galactosidase activity according to the method of Miller (pages 47-55 and 352-355 in Experiments in Molecular Genetics, Cold Spring Harbor Press, New York, N.Y., 1972). Second, fusion protein production simplifies the identification and isolation of the protein product. The fusion protein produced can be easily detected and identified by SDS-polyacrylamide electrophoresis (SDS-PAGE) due to its unique large molecular weight.

Construction of hybrid genes was the approach used in the molecular cloning of genes encoding a number of eucaryotic proteins, such as somatostatin, rat proinsulin, growth hormone, and ovalbumin-like protein. Additionally, procaryotic promoters have been ligated to such fusion protein gene sequences in the case of ovalbumin and $\beta$-globin (Guarente et al., 1980, Cell 20: 543). The Guarente et al. system involves inserting the lac promoter, including the SD sequence, at varying distances in front of the ATG of the fusion protein gene.

To minimize the degradation of the desired proteins which are being produced, it may also be possible to increase the level of gene expression for such fusion proteins. When fusion proteins are produced at high levels in bacterial cells, they tend to form insoluble aggregates within the cell. Stabilization of the aggregate forming proteins can be obtained. These proteins may then be more easily purified from the total host cell proteins. Two reasons may be offered to explain this "stabilization", or minimization of degradation: when high levels of gene expression result in production of the fusion protein in higher than physiological amounts, the insoluble aggregates that form may be more resistant to proteolysis; alternatively, when the proteins are produced at high levels, the host cell's proteolysis system which is responsible for protein degradation may be overwhelmed, and therefore degradation levels are kept at a minimum.

While it may be useful to obtain high levels of host cell production of the fusion protein, it may be more desirable, in some instances to produce large quantities of the unfused protein. For example, the unfused protein may be preferred for use in vaccine formulations, where certain binding sites are required for immunogenicity of the protein. Additionally, production of enzymes as unfused proteins may be necessary to maintain enzymatic activity. However, transformants which produce unfused proteins appear to do so in smaller quantities than transformants which produce fusion proteins; this is true even when the gene sequence of the unfused protein is under control of an inducible promoter. In addition, the unfused protein produced by bacterial transformants may be less stable than fusion proteins. A tremendous utility, therefore, would be afforded by the development of a means to stabilize unfused proteins produced in host cell bacteria.

SUMMARY OF THE INVENTION

M and compositions are provided for the stabilization and purification of eucaryotic, viral or foreign proteins produced in host cell systems. The methods take advantage of the fact that fusion proteins are resistant to degradation in the host cell. The present invention provides for the stabilization of any unfused foreign protein produced in the same host cell which is also producing an aggregate forming protein. This invention is based on the discovery that fusion proteins which are produced at high levels in a host cell tend to form insoluble aggregates within the cell which can be readily purified; and if the same host cell is also producing an unfused protein, the unfused protein will co-aggregate with the fusion protein aggregates. Therefore, stabilization of any unfused protein may be accomplished by modifying a host cell to produce both a fusion protein and an unfused protein. The fusion protein need not be related in any way to the desired unfused protein.

The modification of host cells to produce both a fusion protein and an unfused protein may be accomplished in several ways: (1) a host cell may be co-infected with two or more plasmids. One plasmid should contain the nucleotide sequence encoding the unfused protein (hereinafter referred to as the unfused protein gene) and the other plasmid should contain the nucleotide sequence encoding the fusion protein (hereinafter referred to as the fusion protein gene). Each plasmid should also have its own promoter and other sequences necessary for the host cell to express the genes; (2) a plasmid can be constructed which contains both the fusion protein gene and the unfused protein gene, each with its own promoter and expression control elements; (3) a plasmid containing a fusion protein gene with its own promoter and expression control elements may be modified by the insertion of a nucleotide sequence encoding a chain termination sequence (e.g., amber, ochre, opal) between the desired protein gene and the host gene (e.g., β-galactosidase). This plasmid may then be used to transform a host cell containing the appropriate tRNA suppressor so that both the unfused protein gene and the fusion protein gene are expressed. Finally, methods are described for regulating the production of the fusion protein and the unfused protein. The methods and compositions of the present application are demonstrated for herpes simplex virus (HSV) and bovine growth hormone (BGH).

4. BRIEF DESCRIPTION OF THE FIGURES

The present invention may be more fully understood by reference to the following detailed descriptions of the invention, examples of specific embodiments of the invention, and the appended figures.

In all figures within this text, restriction endonuclease enzyme restriction sites are indicated by the following abbreviations: AccI; BamHI; BglII; EcoRI; EcoRV; HincII; HindIII; PstI; RsaI; SacI; SmaI; XbaI; and XmnI. Restriction endonuclease enzymes themselves are indicated by their typical abbreviations.

Unless otherwise indicated, the figures which follow are not drawn to scale:

FIG. 3 represents the construction of various recombinant plasmids which contain the PPV fusion protein and BGH coding sequences on one plasmid.

5. DESCRIPTION OF THE INVENTION

Figure 1:
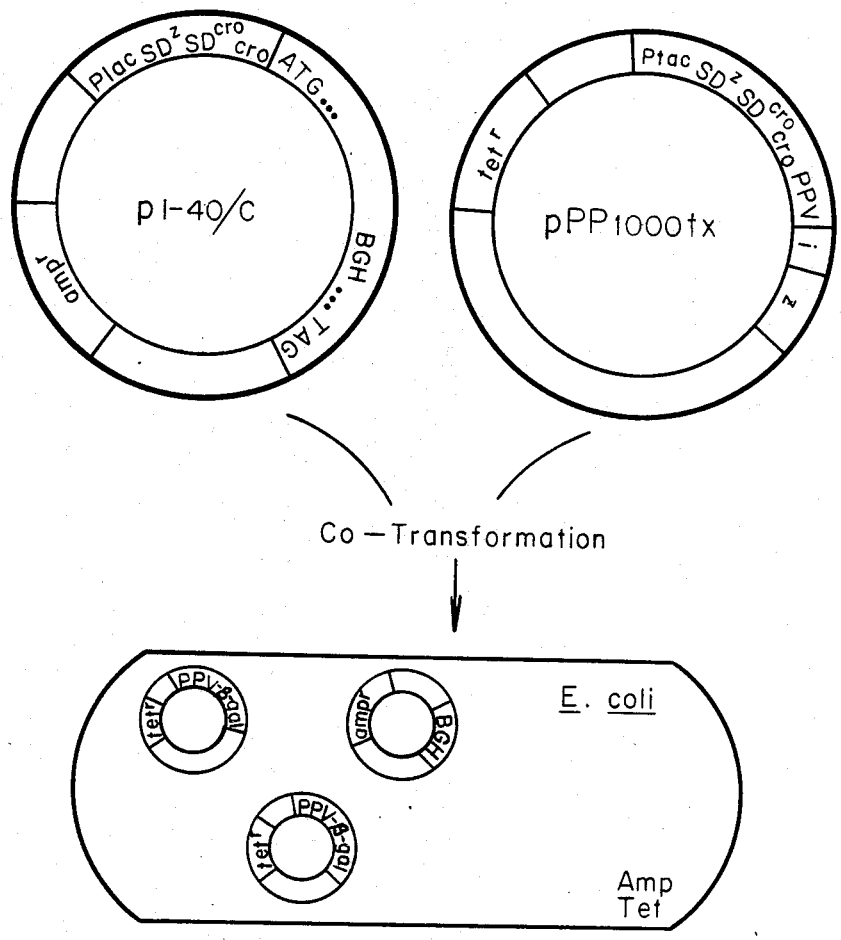
FIG. 1 is a diagrammatic representation of the modified BGH clone pl-40/C and pPP1000tx plasmids which are co-transformed into the host cell. The host cell can now produce both the unfused BGH protein and the Cro/PPV/β-galactosidase fusion protein.

The present invention involves a method for stabilizing and protecting foreign cloned gene products of interest from degradation in transformed cells by co-producing the desired gene product and a fusion protein in the same host cell. The method of this invention provides several advantages over stabilization techniques known in the art. Host cell co-production of the gene product as an unfused protein with fusion proteins protects the gene product from degradation by the host cell proteolytic enzymes and allows for a significant increase in the final yield of product. In addition, the gene product of the present invention forms co-aggregates with aggregate-forming fusion proteins which facilitates purification of the desired gene product. The gene product that aggregates with the fusion protein can be isolated directly from cell lysates or other aqueous protein mixtures by solubilization of the protein aggregates in certain solvents (such as guanidine hydrochloride in water) and subsequent dilution of the protein solution resulting in selective precipitation of the aggregate-forming proteins.

5.1 Preparation of Fusion Proteins

As explained previously, to maximize the level of gene expression in a specific transformant it may be desirable to ligate the gene in question to a gene encoding another protein, such as a host cell protein. The sequences should be in the same translational reading frames and uninterrupted by termination signals. An additional advantage is obtained if the host cell protein inherently contains an assayable function. The expression of the ligated genes results in a fusion protein product that can be identified on the basis of its large molecular weight and assayable function. For example, production of a BGH/β-galactosidase fusion protein offers several advantages for cloning and expression of BGH in an *E. coli* host. First, this allows for an approximation of the level of protein production (hence expression) directed by the vector using a colorimetric assay specific for β-galactosidase activity according to the method of Miller (pages 47–55 and 352–355 in Experiments in Molecular Genetics, Cold Spring Harbor Press, New York, N.Y., 1972). Second, fusion protein production simplifies the identification and isolation of the protein product. The unfused BGH protein is smaller than the BGH/β-galactosidase fusion protein. The unfused BGH protein may co-migrate with several other host cell proteins when analyzed by SDS-polyacrylamide gel electrophoresis. However, the fusion protein produced can be easily detected and identified by SDS-polyacrylamide electrophoresis (SDS-PAGE) due to its unique large molecular weight.

The present invention is not limited to the production of a β-galactosidase fusion protein; any gene of either eucaryotic or procaryotic origin may be ligated in phase with a second gene to provide advantages similar to the β-galactosidase fusion protein product. Examples include, but are not limited to, galactokinase; trp D, E or leader; pilus genes; and eucaryotic genes, such as thymidine kinase, β-globin, SV-40 T-antigen, or Rous Sarcoma Virus transforming gene.

In order to construct a gene which encodes a fusion protein, the two genes must be joined within their coding sequence such that the translational reading frame is maintained and uninterrupted by termination signals. Also, as previously explained, if the host cell is a strain which inhibits the action of the promoter, the fusion protein will be produced only in response to induction.

5.2. Preparation of Both Fused and Unfused Proteins

As previously explained, transformants which produce unfused proteins, generally appear to do so in smaller quantities than transformants which produce fusion proteins; this is true even when the gene sequence for the unfused protein is under the control of an inducible promoter. The unfused proteins produced by bacterial transformants may be less stable than fusion proteins. In an alternate embodiment of the present invention, a host cell transformant can be engineered to produce large quantities of both fused and unfused proteins which will co-aggregate and can be purified easily.

According to the method of this invention, the desired gene product may be co-produced with a fusion protein in the same host cell by a number of methods. For example, the host cell can be transformed with two different expression plasmids, one carrying the desired protein gene and one carrying the fusion protein gene; alternatively both the desired protein gene and the fusion protein gene may be inserted into a single expression plasmid; or the fusion protein gene itself may be modified so that both the unfused protein and the fusion protein are produced in a single host. These methods are described in Sections 5.2.1., 5.2.2., and 5.2.3. The present invention also allows for the regulation of the ratio of expression of the fusion protein and the desired gene product. Regardless of the method used to co-express the genes in one host cell, the unfused protein and the fusion proteins co-purify when using the aggregate purification procedure described in Section 5.5. After solubilization of the aggregate proteins, the unfused protein can be separated from the fusion protein on the basis of size or charge. As a result, large quantities of an unfused protein produced by host cell transformants can be easily purified.

For the following exemplary embodiments, any cells capable of expressing the genes for and producing aggregate-forming proteins are suitable as hosts. Aggregate-forming proteins produced in E. coli studied during the development of this invention include β-galactosidase, trpE, reverse transcriptase, bovine growth hormone, herpes simplex gD-fusion proteins, porcine parvovirus fusion proteins, canine parvovirus fusion proteins, bovine papilloma virus fusion proteins, and pseudorabies virus fusion proteins.

5.2.1. Co-Transformation of Host Cells

This embodiment of the present invention involves the co-transformation of any appropriate host cell with two or more plasmids. One plasmid carries the desired unfused protein gene and one plasmid carries a fusion protein gene. Each gene should be under the control of a promoter. The same or different promoter systems may be used to control synthesis of each gene. If a different promoter is used for each gene sequence, the ratio of the expression of the sequences may be controlled by varying the degree of induction of each promoter. Efficiency of expression of either or both genes may be improved by the addition of other expression control elements. Such elements include but are not limited to those previously described in Section 2.1.

In addition, the two plasmids may carry different selectable drug markers for antibiotic resistance (e.g., tetracycline and ampicillin resistance) and may be maintained within the same cell if grown in the presence of the two antibiotics. With both plasmids in the cell, synthesis of the fusion protein and the labile unfused protein can occur.

These transformed cells produce insoluble aggregates which contain both the unfused proteins and the large fusion protein. Any combination of fusion protein with unfused protein will have the aggregation and stabilization properties.

5.2.2. Transformation of Host Cells with One Plasmid Carrying Two Genes

In another embodiment of the present invention, plasmids which carry both the unfused protein gene and the larger fusion protein gene on a single vector are designed and constructed. As described supra for the co-infection scheme, this invention is suitable for any combination of fusion protein and any unfused protein.

The plasmids are constructed such that each gene on the plasmid is under the control of a promoter. The same or different promoter systems may be used to control expression of each gene, therefore this embodiment of the present invention also allows for the regulation of the ratio of the fusion protein and the desired gene product. The efficiency of expression of either or both genes may be further regulated by the addition of expression control elements including but not limited to those previously discussed in Section 2.1. In addition, the plasmid may carry a single selectable drug marker for antibiotic resistance.

A significant stabilization of the unfused protein is observed when both genes are included on one plasmid. Again, since both proteins are produced in the same cell, aggregation of the larger fusion protein also causes the smaller unfused protein to complex with the aggregate. Therefore, stabilization and hence purification of significant amounts of the unfused proteins can be realized.

5.2.3. Modification of the Fusion Protein Gene

In an alternate embodiment of the present invention, a recombinant plasmid which encodes a fusion protein is altered at the junction of the two gene sequences which comprise the fusion protein gene. A chain termination sequence such as amber (TAG), ochre (TAA), or opal (TGA) is located in between the two gene sequences; the chain terminator must be in phase with the translational reading frames of both gene sequences. Such an alteration may be accomplished by cleaving the plasmid at a restriction site (or sites) located in between the two gene sequences and then ligating a nucleotide linker sequence encoding a chain terminator such as amber, ochre, or opal into the cleaved site on the plasmid so that the chain terminator is in phase with the translational reading frames of both gene sequences.

Introduction of these amber, ochre, or opal modified plasmids into a host cell containing the appropriate tRNA suppressors results in the synthesis of both an unfused protein as well as a fusion protein (because suppression is significantly less than 100%). A tRNA suppressor is encoded by a tRNA gene that has undergone a mutation that allows the tRNA to recognize the termination codon and results in the occasional but not regular insertion of an amino acid under the direction of the termination codon. Therefore, host cells carrying the suppressor tRNA characteristically produce both the unfused protein and a fusion protein of normal length. Every nonsense or termination suppressor has a characteristic efficiency, indicated by the fraction of protein chains that are completed.

There are at least two ways to introduce the amber, ochre or opal modified plasmids into a suppressor cell background: (1) the transformant (i.e., a host cell transformed with amber, ochre or opal modified plasmid) can be infected with a lysogenic transducing phage that carries the appropriate suppressor tRNA gene (e.g., ⌀80 pSU3 carries the supF suppressor of amber mutations); or (2) the amber, ochre or opal modified plasmids can be used to transform cell lines which contain suppressor tRNAs of amber, ochre, or opal respectively. Examples of such strains include but are not limited to LE392 (containing supE and supF suppressors of amber mutations), YMC (containing supF), and C600 (containing supE). The various amber suppressor tRNA genes in E. coli include but are not limited to: supB, supC, supD, supE, supF, supG, supL, supM, supN, supO, supP, supU, supV; the various ochre suppressor tRNA genes in E. coli include but are not limited to: supB, supC, supG, supL, supM, supN, supO, supV; and the various opal suppressor tRNA genes in E. coli incude but are not limited to: supK (see Bachmann and Low, 1980, Microbiological Reviews 44(1): 1-56).

The host cells containing the appropriate suppressor tRNA gene are transformed with the amber, ochre, or opal modified plasmids and can produce the protein as both a fusion protein and as an unfused protein (the proportions of fused to unfused protein produced depends upon the extent of suppression in the host cell).

The amber, ochre, or opal modified plasmids may be further modified to ensure that translation of the corresponding mRNA transcript will terminate at the 3'-terminus of the fusion protein gene. Proper chain termination is important because it contributes to the overall efficiency of translation. A number of approaches which may be used to effect chain termination are described below. In one embodiment, all three chain termination sequences may be inserted in tandem at the 3'-region of the fusion protein gene so that they are in phase with the translational reading frame of the gene sequence. The presence of the chain terminator sequences in tandem will reduce the chance of read-through, consequently, translation will terminate at the chain termination codons on the mRNA transcript.

Alternatively, one or more chain termination sequences of the appropriate type may be inserted into the 3'-region of the fusion protein gene. For example, an amber modified plasmid may be further modified by the insertion (in phase) of one or more opal or ochre sequences at the 3'-end of the fusion protein gene. When this plasmid is inserted into a host cell containing an amber tRNA suppressor (such as supD, supE, supF, supP, supU, supV in E. coli) that does not suppress ochre or opal, the host cell will produce both the fusion protein and the unfused protein and translation of the fusion protein will terminate at the location of the opal and/or ochre codons located at the 3'-end of the mRNA transcript.

In a similar fashion, an opal modified plasmid may be further modified by the insertion (in phase) of one or more amber or ochre sequences at the 3'-end of the fusion protein gene. When this plasmid is inserted into a host cell containing an opal tRNA suppressor (such as supK in E. coli) that does not suppress amber or ochre, the host cell will produce both the fusion protein and the unfused protein and translation of the fusion protein will terminate at the location of the amber and/or ochre codons located at the 3'-end of the mRNA transcript.

Similarly, an ochre modified plasmid may be further modified by the insertion (in phase) of one or more opal sequences at the 3'-end of the fusion protein gene. When this plasmid is inserted into a host cell containing an ochre tRNA suppressor (such as supB, supC, supG, supL, supM, supN, supO, supV in E. coli) that does not suppress opal, the host cell will produce both the fusion protein and the unfused protein and translation of the fusion protein will terminate at the location of the opal codon (or codons) located at the 3'-end of the mRNA transcript.

5.3. Regulation of Production of Fusion Protein and Unfused Proteins

Since the fusion protein is a by-product of the present invention (in the sense that one may be interested only in recovery of the unfused protein), it may be desirable to limit the production of fusion protein and, moreover, to increase the production of the unfused protein. In this way cellular energy is not unnecessarily wasted. Limitation of expression of the fusion protein gene can be accomplished in several ways. For example, expression can be controlled at the level of transcription and translation. Accordingly, in host cells co-transformed with two plasmids (see Section 5.2.1.) or with one plasmid containing both genes (see Section 5.2.2.), the production of fusion protein may be limited by preceding the fusion protein gene with a weak promoter and preceding the unfused protein gene with a strong promoter.

To obtain efficient expression of a gene (or a portion of the gene), a promoter located 5' to the inserted gene must be present in the expression vector. RNA polymerase normally binds to the promoter and initiates transcription of a gene or a group of linked genes and regulatory elements. This group is called an operon. Promoters vary in their "strength", i.e., their ability to promote transcription and thus produce large quantities of gene product. Depending upon the host cell system utilized, any one of a number of suitable promoters may be used. For instance, when cloning in an E. coli, its bacteriophages or plasmids promoters such as the lac promoter, trp promoter, recA promoter, ribosomal RNA promoter, the $P_R$ and $P_L$ promoters of coliphage lambda and others including but not limited to lacuv5, trp-lacuv5 (tac) hybrid promoter, ompF, bla, lpp and the like, may be used to direct high levels of transcription of adjacent DNA segments. Additionally, E. coli promoters produced by recombinant DNA or other synthetic DNA techniques may be used to provide for transcription of the inserted gene.

When cloning in a eucaryotic host cell, enhancer sequences (e.g., the 72 b.p. tandem repeat of SV40 DNA, retroviral long terminal repeats or LTRs, etc.) may be inserted to increase transcriptional efficiency. Enhancer sequences are a set of eucaryotic promoter elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have a remarkable ability to function upstream from, within, or downstream from eucaryotic genes; therefore, the position of the enhancer sequence with respect to the inserted gene is less critical.

Specific initiation signals are also required for efficient translation in procaryotic and eucaryotic cells. Protein synthesis is initiated as the result of interaction between two mRNA sites: the ribosome binding site (SD sequence on the DNA) and the initiation codon AUG (ATG on the DNA ). These translation initiation signals may vary in "strength" as measured by the quantity of gene specific protein synthesized. The DNA expression vector, in addition to containing a promoter for transcription, may also contain any combination of various "strong" translation initiation signals. Thus, any SD-ATG combination that can be utilized by host cell ribosomes may be employed; such combinations include, but are not limited to, the SD-ATG combination from the cro gene or the N gene of coliphage lambda, or from the E. coli tryptophan E, D, C, B, or A genes. Additionally, any SD-ATG combination produced by recombinant DNA or other synthetic technique may be used.

Any of the methods previously described for the insertion of DNA fragments into a vector may be used to ligate a promoter and other control elements into specific sites within the vector.

Accordingly, a gene (or any portion thereof) can be ligated into an expression vector at a specific site in relation to the vector promoter and control elements so that the gene sequence is in the correct translational reading frame (i.e., in phase) with respect to the vector ATG sequence. Alternatively, the vector and/or gene sequence may be modified so that the ATG (or GTG or CTG) of the gene sequence is used as the initiation signal. The resultant recombinant DNA molecule is then introduced into appropriate host cells by transformation, transduction or transfection (depending on the vector/host cell system). Transformants are selected based upon the expression of appropriate gene markers normally present in the vectors, such as ampicillin resistance or tetracycline resistance in pBR322, or thymidine kinase activity in eucaryotic host systems. Expression of such marker genes indicates that the recombinant DNA molecule is intact and is replicating. Expression vectors may be derived from cloning vectors, which usually contain a marker function; such cloning vectors may include, but are not limited to the following: SV40 and adenovirus vectors, yeast vectors, bacteriophage vectors such as lambda gt-WES-lambda B, Charon 28, Charon 4A, lambda gt-1-lambda BC, lambda gt-1-lambda B, M13mp7, M13mp8, M13mp9, or plasmid DNA vectors such as pBR322, pAC105, pVA51, pACYC177, pKH47, pACYC184, pUB110, pMB9, pBR325, Col El, pSC101, pBR313, pML21, RSF2124, pCR1 or RP4.

In some cases, as in the lactose and tryptophan operon systems, the promoter regions are overlapped by "operator" regions to form a combined "promoter-/operator" sequence. Operators are DNA sequences which are recognized by the repressor proteins of a particular operon, which serve to regulate the frequency of transcription initiation in a particular promoter. In recombinant DNA studies, these promoter-/operator systems are used in order to produce a large number of mRNA transcripts, and, therefore, large amounts of a desired gene product (e.g., BGH, interferon, enzymes). The relative "strength" or efficiency of these promoters will in part, determine the overall expression/production of a desired protein product. However, it would be advantageous if gene expression could be "turned-on" and "turned-off" at a desired time-point. Such control is an attractive feature where large scale fermentation is concerned. Therefore, the ideal promoter/operator system is one that has a very powerful promoter system and also is easily controlled.

To control gene expression, host cell strains may be chosen which inhibit the action of the promoter unless specifically induced. In this way, greater than 95% of the vector's promoter's effectiveness may be inhibited in uninduced cells. As previously explained, in certain operons the addition of specific inducers is necessary for efficient transcription and translation of the inserted DNA; for example, the lac operon is induced by the addition of lactose or IPTG (i.e., isopropylthio-β-D-galactoside). A variety of other operons, such as trp, pro, etc., are under different controls. The trp operon is induced when tryptophan is absent in the growth media; and the $P_L$ promoter of lambda is induced by an increase in temperature in host cells containing a temperature sensitive lambda repressor protein, e.g., cI857. Thus, expression of the genetically engineered unfused protein may be controlled. This is important if production of the protein product of the cloned gene is lethal or otherwise detrimental to the host cells. In such cases, the foreign gene may be replicated but not expressed during growth of the transformants. After the cells reach a suitable density in the growth medium, the promoter can be induced for production of the protein.

One such promoter/operator system is the trp-lac promoter/operator system (referred to as "tac"). This hybrid promoter is constructed by combining the −35 b.p. (−35 region) of the trp promoter and the −10 b.p. (−10 region or Pribnow box) of the lac promoter (the sequences of DNA which are the RNA polymerase binding site). In addition to maintaining the strong promoter characteristics of the tryptophan promoter, tac is also easily controlled by the lac repressor (from lac I$^q$). This construction may explain the higher efficiency of expression of this hybrid promoter with respect to either one of the parental promoters.

Gene expression can also be controlled at the level of translation. In host cells transformed with amber, ochre, or opal modified plasmids (See Section 5.2.3.), translation of the mRNA produced from the plasmid DNA stops at the nonsense codon and only the desired protein (unfused) is expressed. In an appropriate host (one that is able to "suppress" the nonsense codon), some of the ribosomes, "read through" the nonsense codon and synthesize fusion protein. Since the level of suppression varies in different host cells, it is possible to regulate the ratio of unfused protein to fusion protein by choosing the appropriate suppressor host cell.

The expression of genes maybe regulated in several other ways. For example, in order to improve the initiation of translation, an A/T DNA segment may be inserted between the $SD^{cro}$ and the ATG initiator sequence for the start of translation. An oligomer which contains an A/T rich sequence may be synthesized using state-of-the-art nucleic acid chemistry. A particularly useful method is described in U.S. patent application Ser. No. 491,099 by Kempe, et al., filed May 5, 1983 which is incorporated herein by reference. This A/T rich segment may be needed to destabilize the secondary structure of the mRNA within this region and thereby facilitate ribosome binding and subsequent translation along the message.

In many recombinant plasmids studied only one translational stop codon (e.g., TAG, TAA or TGA) is present for termination of translation, and no transcriptional-stop like sequences are found in the 3' untranslated region of the DNA. Therefore, a synthetic oligomer containing a triple translational stop sequence, with all 3 chain termination codons may be inserted in phase with the reading frame of the protein gene. Again, this linker may be synthesized using methods referred to above. This construction should then provide for efficient termination of translation by assuring proper translational termination with little chance of read-through into the untranslated region of the mRNA.

Recent studies have shown that the tryptophan attenuator region of the tryptophan operon provides for the efficient termination of the mRNA transcript from the DNA. This extremely stable stem and loop structure is characteristically GC-rich, possesses dyad symmetry, and is followed by an oligo-(T) stretch at the site of termination similar to the well known features of rho-independent transcription termination sites in procaryotes. By taking advantage of this system, a sequence coding for the attenuator portion of the tryptophan operon may be placed 3' of the translational stop codons of the genome. This construction may now allow for the effective termination of transcription of the mRNA.

The regulation of expression of any protein includes, but is not limited to the construction and use of promoter/operator systems, A/T rich sequences, transcriptional and translational termination sequences, and any other constructions (either naturally occurring or synthetically made) which provide an "optimal" system for expression of a protein in a compatible host cell.

The present invention includes, but is not limited to the production of fusion proteins encoded by genes containing the following components: β-galactosidase, galactokinase; trp D, E or leader; pilus genes; and eucaryotic genes, such as thymidine kinase, β-globin, SV-40 T-antigen, or Rous Sarcoma Virus transforming gene.

5.4. Identification of the Gene Product

Identification of the protein described in this invention is based upon two requirements. First, the protein should be produced only in response to the induction of the promoter. Second, the protein can be detected immunologically using a variety of polyclonal or monoclonal antibodies directed against the protein; if the protein is to be used in vaccine formulations the protein should be immunoreactive whether it results from the expression of the entire gene sequence, a portion of the gene sequence or from two or more gene sequences which are ligated to direct the production of a fusion protein. This reactivity may be demonstrated by standard immunological techniques, such as immunoprecipitations, immunodiffusion, radio-immune competition, immunoelectrophoresis or the immunological detection of proteins which were separated by polyacrylamide gel electrophoresis and then transferred to nitrocellulose.

5.5. Purification of Aggregate Forming Proteins

Cells containing the cloned gene are grown up in a large volume, and the proteins produced after induction of the promoter are isolated from such cells. The proteins may be isolated and purified either by standard chromatography including ion exchange, affinity or sizing resins, by centrifugation, or by any other standard technique for the purification of proteins.

Since certain fusion proteins form aggregates when overproduced in cells and when in solution and will co-aggregate with unfused protein, a method for isolating aggregate-forming proteins is particularly useful for isolating the fusion proteins and unfused proteins produced in the present invention. Purification of aggregate proteins (hereinafter referred to as aggregate purification) involves the extraction, separation and/or purification of aggregate-forming proteins by disruption of cells followed by washing the aggregated material. Additionally, the aggregated material may be solubilized by the addition of a solvent that is both a strong hydrogen acceptor and a strong hydrogen donor (or a combination of solvents each having one of these properties); the aggregate-forming proteins may then be precipitated by dilution with a compatible buffer. Suitable protein solvents include, but are not limited to urea (from about 4M to about 8M), formamide (at least about 80%, volume/volume basis), and guanidine hydrochloride (from about 4M to about 8M). Some solvents which are capable of solubilizing aggregate-forming proteins, for example SDS (sodium dodecyl sulfate), 70% formic acid, are inappropriate for use in this procedure due to the possibility of irreversible denaturation of the proteins, hence a lack of immunogenicity and/or activity. Although guanidine hydrochloride and similar agents are denaturants, studies indicate that this denaturation is not irreversible and that renaturation may occur upon removal (by dialysis, for example) or dilution of the denaturant, allowing re-formation of immunologically and/or biologically active protein.

One embodiment of the fusion protein isolation technique is outlined as follows (hereinafter referred to as the non-denaturing aggregate purification procedure): the cell pellet is quick frozen using dry ice/methanol, weighed, and 3–4 g of cells are resuspended in at least 25 ml of a buffer solution [e.g., 50mM Tris-HCl (tris hydroxymethylaminomethane-hydrochloride), pH 8.0, 2mM EDTA (ethylenediaminetetraacetic acid) and 200mM NaCl]. That is, the cells are suspended in a buffer solution at an approximate concentration of from about 100 to 200 grams of cells/liter. Concentrations less than about 160 grams/liter are preferred. To this suspension lysozyme is added to a final concentration of about 130 µg/ml and the resulting mixture is allowed to stand at 4° C. for 20 minutes with occasional shaking. Nonidet P40 (NP-40, Shell trademark, polyoxyethylene (9) p-tert-octylphenol), a non-ionic detergent used to solubilize membranes, is added to a final concentration of about 0.1% and the solution mixed. Then, the suspension is ground for approximately 1 minute using a Polytron grinder (Brinkman Instruments, Westbury, N.Y.) or equivalent.

The suspension is centrifuged at 8,000 ×g for 30 minutes, and the pellet resuspended in a wash buffer, e.g., 20mM Tris-HCl (pH 7.2), 1mM EDTA, 150mM NaCl and 2% Triton-X 100 (polyoxyethylene (9–10) p-tert-octylphenol, a non-ionic detergent), and ground with the Polytron grinder. This step of centrifugation, washing, and grinding may be repeated to further wash the pellet and remove as much cellular debris as possible. This pellet of aggregates may be resuspended in an appropriate buffer (e.g. Phosphate Buffered Saline: 20mM sodium phosphate, pH 6.8, 150mM NaCl) and used directly.

Alternatively, the pellet of aggregates may be further treated by the addition of a denaturant (hereinafter referred to as the denaturing aggregate purification procedure) as follows: the suspension is centrifuged, the supernatant removed completely and the pellet resuspended in about one-fifth volume of 6M guanidine hydrochloride (in distilled water). For instance, 3 g of cells washed with 25 ml of buffer should be resuspended at this step in 5 ml of 6M guanidine hydrochloride solution. It may be difficult to resuspend the pellet at this stage and sonication or homogenization may be required in order to obtain a homogenous solution. The solution is allowed to stand at 22° C. for 20 minutes and is then centrifuged at 8,000 ×g for 30 minutes to remove debris, saving the supernatant which at this point contains the fusion protein and the unfused protein.

It may be desirable to remove any remaining DNA from the suspension of aggregates or the fusion protein precipitate before using either as an immunogen. To this end, the suspension of aggregates or fusion protein precipitate is pelleted and resuspended in wash buffer containing no detergent. To either suspension a final concentration of about 10 mM $MgCl_2$ and 2µg/ml Deoxyribonuclease I (P.L. Biochemicals, Milwaukee, WI.) is added. After incubation at 37° C. for 30 minutes, the suspension of aggregates or fusion protein precipitate is pelleted by centrifugation, washed with buffer, repelleted, and resuspended in fresh buffer, thus removing most of the deoxyribonuclease.

After solubilization, the unfused protein can be separated from the fused protein by standard separation techniques.

6. EXAMPLES

According to the method of the present invention, the unfused protein gene is inserted into a plasmid and is expressed along with a gene encoding an aggregate-forming protein (e.g., a fusion protein). As explained in Section 5, this may be accomplished by transforming a host cell with two plasmids, each containing either the unfused protein gene or the fusion protein. The method of the present invention also includes inserting the unfused protein gene and the fusion protein gene in the same plasmid. This can also be accomplished by ligating the desired protein with a host cell protein (e.g., *E. coli* β-galactosidase) and separating the two genes coding for the proteins by a nucleotide linker encoding a chain termination sequence. By transforming a suppressor *E. coli* with the plasmid, the desired protein can be produced at a higher rate than the fusion protein.

For the purposes of the present invention, plasmids were utilized which direct the production of various protein products including but not limited to: porcine parvovirus (PPV) which is described in U.S. patent application Ser. No. 564,567 by Halling et al., filed Dec. 22, 1983; bovine growth hormone (BGH) which is described in U.S. patent application Ser. No. 548,917 by George et al., filed Nov. 7, 1983, now abandoned; and herpes simplex virus (HSV) which is described in U.S. patent application Ser. No. 510,551 by Watson et al., filed July 6, 1983 which are incorporated herein by reference.

6.1. Construction of Plasmids which Produce Aggregate-Forming Proteins

Various plasmids were constructed to carry and express the unfused BGH or HSV protein, the larger Cro/PPV/β-galactosidase fusion protein and/or the Cro/HSV/β-galactosidase fusion protein.

6.1.1. Co-Tranformation with BGH Plasmid and Fusion Protein Plasmid

In this embodiment of the present invention, two plasmids were used to co-transform *E. coli* bacterial cultures Plasmid pPP1000tx (see FIG. 1) was constructed to encode the Cro/PPV/β-galactosidase fusion protein. This plasmid carried the gene for tetracycline resistance, therefore bacteria transformed with this plasmid were both tetracycline resistant and produced Cro/PPV/β-galactosidase fusion protein.

Plasmid DNA from BGH clone pl-40/C contained the gene sequences that code for unfused modified BGH protein (See FIG. 1). This plasmid also contained the gene sequences that code for ampicillin resistance. Hence, bacteria which were transformed with this plasmid were resistant to ampicillin and also produced the modified BGH protein.

6.1.2 Transformation of *E. coli* and Expression of Fusion Proteins

Both the PPV and BGH recombinant plasmids were used to co-transform *E. coli* strain NF1829. Transformants were plated onto Luria broth plates containing both ampicillin (100 μg/ml) and tetracycline (20 μg/ml). By having different selectable drug markers on each respective plasmid, both plasmids were maintained within the cell in the presence of the two antibiotics.

Single colony isolates were selected and assayed for the production of both fusion protein and the unfused BGH protein. Two approaches were used to analyze the proteins produced: direct analysis of total lysates of cells by SDS-PAGE analysis and/or specific immunoprecipitation.

6.1.3 Stabilization of Unfused BGH Protein

A significant stabilization of the unfused BGH protein was observed when both plasmids were in the cell, each synthesizing their respective proteins. Pulse-chase experiments indicated that the half-life of the unfused modified-BGH proteins had increased from a 1–2 minute level to between 30 minutes and 1 hour. Additionally, when these genes were highly expressed within the cell, they formed insoluble aggregates which contained both the unfused BGH protein and the large Cro/PPV/β-galactosidase fusion protein. Subsequent purification of the aggregate proteins indicated that the protein could be obtained in gram quantities.

The Cro/PPV/β-galactosidase fusion protein was estimated to be present at approximately 10% of the total bacterial cell protein whereas unfused modified BGH protein from clone pl-40/C was estimated to be present at about 1–2% of the total cell protein. Estimates were made from total cell protein lysates analyzed by SDS-PAGE and quantitatively scanned by densometric methods.

Purification from 1 liter of shaker flask cultures yielded approximately 1.5–2.0g dry weight cells. Purification of fusion and unfused aggregate proteins yielded approximately 0.1 to 0.2g per liter of cells.

6.1.4. Insertion of BGH into PPV Fusion Protein Plasmid

Due to the possible instability associated with using separate plasmids within the cell to carry and express the genes encoding the unfused BGH protein and the larger fusion protein, various plasmids which carry both genes on only one vector, each with its own promoter and translational start sequences were constructed.

Figure 2:
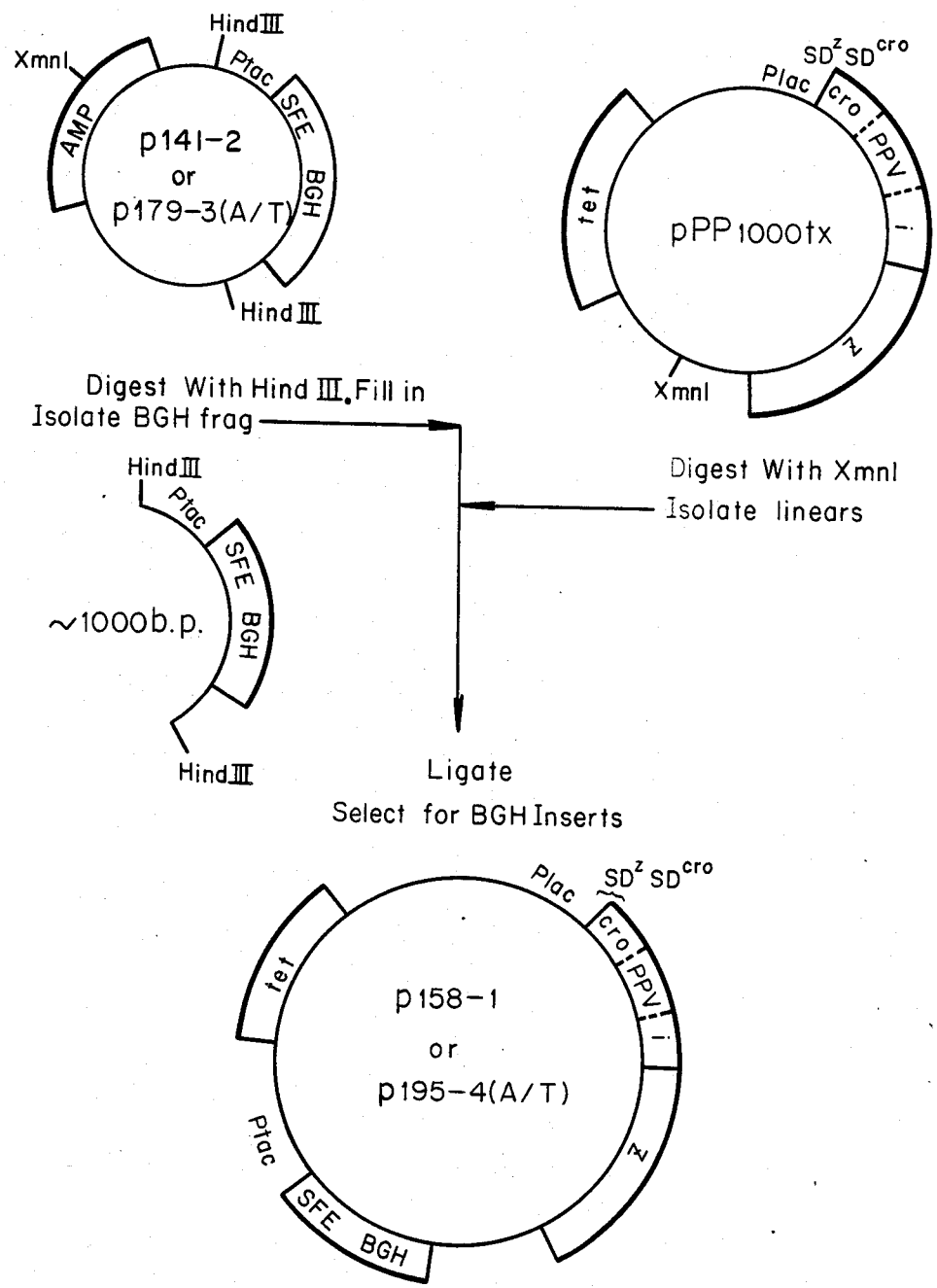
FIG. 2 is a schematic diagram which represents the construction of ptac-BGH clones p158-1 and p195-4 which contain synthetic front end sequences (SFE). The recombinant plasmids direct the production of both BGH protein and Cro/PPV/β-galactosidase fusion protein.

For example, the ptac-BGH sequences from plasmids p141-2 and p179-3 were ligated to the pPP1000tx plasmid as described in FIG. 2. Plasmids p158-1 and p195-4 were isolated and assayed for the production of both the Cro/PPV/β-galactosidase fusion protein and the BGH protein.

The ptac-SFE-BGH-TTS-trp attenuator sequences from plasmid p214-1 was ligated to the pPP1000tx plasmid as described in FIG. 3. Plasmid p231-3 was isolated and assayed for the production of Cro/PPV/β-galactosidase fusion protein and the BGH protein.

The ptac-A/T-BGH-TTS-trp attenuator sequences from p217-1 were ligated to the pPP1000tx plasmid and several clones, including p230-2/3, p230-5/3, and p230-6/2 and p231-3 were isolated and assayed for the production of both the Cro/PPV/β-galactosidase fusion protein and the BGH protein.

6.1.5. Analysis of Proteins Produced by Transformants

PPV recombinant plasmids were used to transform *E. coli* strain NF1829, SK107, F'SK107, or LE392.

Transformants were isolated and their plasmids assayed by restriction analysis for the insertion of the fragment. Clones which were positive for the insert were then assayed for the production of both the Cro/PPV/β-galactosidase fusion protein and the BGH protein after induction of the promoter with IPTG or lactose.

A number of clones were identified as expression positive for both proteins. Furthermore, a significant amount of stabilization of the BGH protein described supra was evident. Purification of the aggregate proteins also enabled the purification of the unfused protein.

The unfused protein and fusion proteins produced by E. coli transformants were isolated and purified by the non-denaturing co-aggregate purification method which is outlined in detail in Section 5.5, supra. Briefly, L-broth containing, as appropriate, either 100 μg/ml ampicillin and/or 20 μg/ml tetracycline and 1% lactose or lmM IPTG was inoculated with selected transformants. After incubation at 30° C. overnight the cells were pelleted and quick frozen in dry ice/methanol. The unfused protein and fusion protein were then isolated according to the embodiment described in Section 5.5. The unfused protein can be separated from the fusion protein on the basis of size or charge.

The isolated co-aggregate proteins were resuspended in 50 μl distilled H₂O to which 50 μl of 2× Sample Buffer (2× Sample Buffer is composed of 10% SDS, 40mM Tris-HCl, pH6.8, 2% B-ME, and 0.02 volumes saturated solution of bromphenol blue) was added and mixed well. The mixture was boiled for 5 minutes and 25 μl aliquots were applied to 10% SDS-polyacrylamide gels. The bacterial strains synthesized polypeptides of the sizes predicted for fusion or unfused BGH protein: PPV/β-galactosidase fusion protein—120,000 daltons; unfused BGH protein, 22,000 daltons (modified BGH) and 21,000 daltons (pl-40/c protein).

After SDS-PAGE, the unfused protein was present in sufficient quantity to form a prominent band. The protein can therefore be isolated and purified from the larger aggregate forming protein by standard separation techniques (eg., gel filtration, electrophoresis, and chromatographic procedures). Amino acid analysis of this band was performed using state-of-the-art techniques to confirm that this protein was indeed the desired product (Hirs, (ed.): "Amino Acid Analysis and Related Procedures," Sec. 1 in Methods in Enzymology, vol. II, Academic, New York, 1967).

6.1.6. Quantitation of Protein

Analysis via SDS-PAGE indicated that in clones which contain and produce the PPV/β-galactosidase fusion protein that approximately 10% of the total bacterial cell protein was fusion protein and up to 18% of the total cell protein was unfused BGH protein.

The minimum amount of expression need to cause aggregation of the fusion protein is probably dependent on the nature of the fusion protein utilized. For several BGH-PPV/β-galactosidase fusion constructs, a significant amount of expression (greater than 3%) was required to cause the co-aggregation of these unfused protein and fusion protein.

6.1.7 Construction of Herpes Simplex Virus Plasmide which Produces Both Cro/gD-1 and Cro/gD-1/β-Galactosidase Fusion Protein The HSV glycoprotein (gD) gene may be obtained from any HSV type 1 or type 2 strain.

The construction of these recombinant plasmids provides for host cell production of a protein which is a gD-related polypeptide and which is stable and resistant to host cell degradation; such plasmids enable host cell generation of large quantities of a gD-related protein or fusion protein containing immunological and antigenic determinants of gD proteins.

Figure 4A:
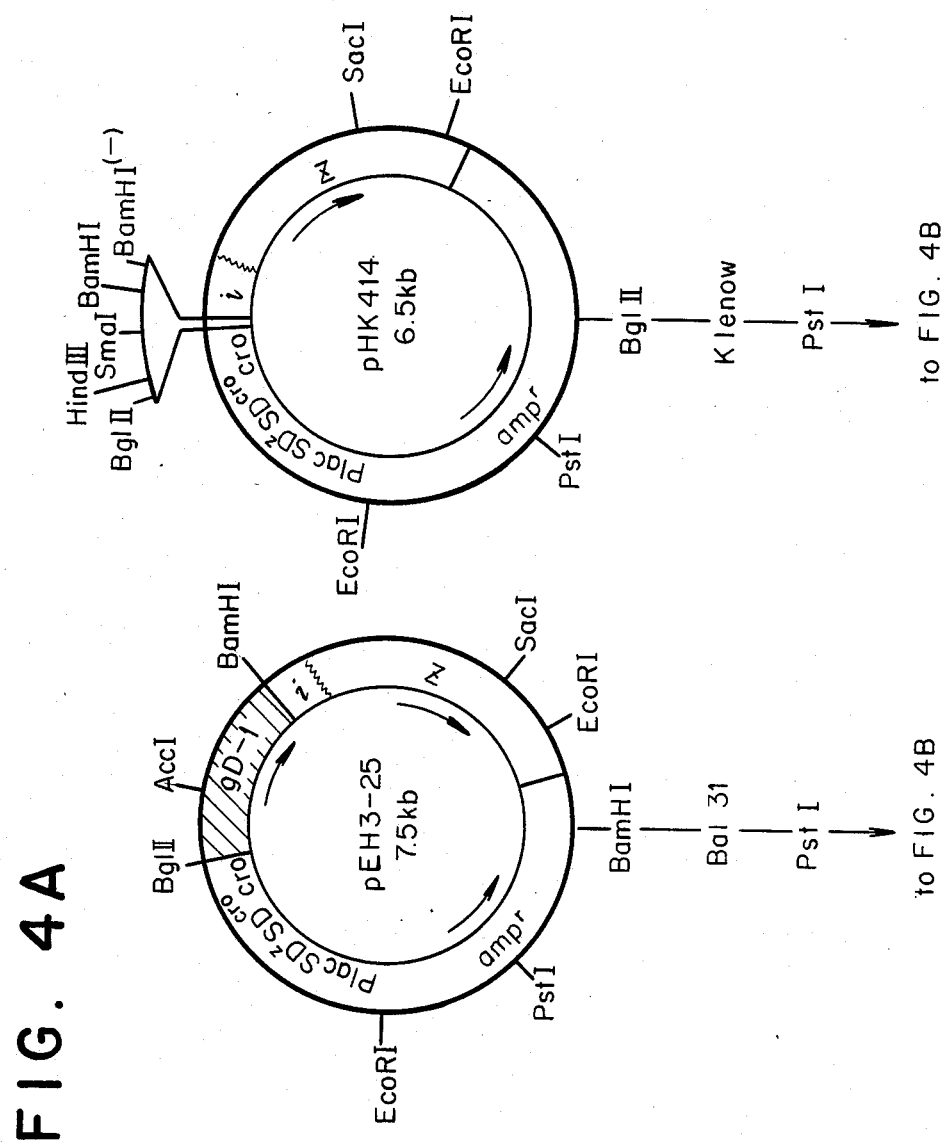
FIG. 4A represent 4B the construction of pEH90-10am, a gD-1 expression plasmid derived from pEH3-25 and pHK414. The recombinant plasmid, pEH90-10am, allows for the production of gD-1 both fused and unfused to β-galactosidase in *E. coli* transformants containing amber suppressor tRNAs.

A recombinant plasmid, pEH90-10am was constructed which can direct the production of both a fused and unfused gD-1 related protein in appropriate host cells (see FIGS. 4A and 4B).

Recombinant plasmid, pEH-90-10am, contains an amber chain termination sequence (TAG) in phase with the translational reading frames of both the gD-1 gene and the i-z-gene.

When pEH90-10 am was used to transform E. coli NF1829, the ampicillin resistant transformants synthesized no detectable fusion protein. However, when the pEH90-10am transformant was infected with the lysogenic transducing phage, ⌀080 SuIII, carrying an amber suppressor tRNA gene, then the induced transformants produced a Cro/gD-1/β-galactosidase fusion protein and a Cro/gD-1 unfused protein. The lysogens are designated pEH90-10am SuIII.

Alternatively, the pEH90-10am plasmid was used to transform E. coli LE392 which carries two amber suppressor mutations (supE and supF). The pEH90-10am LE392 transformants produced a Cro/gD-1/B-galactosidase fusion protein under both induced and non-induced conditions. (LE392 cells do not have the lac I$^q$ mutation of NF1829 which results in overproduction of lac repressor). SDS-PAGE analysis of the proteins produced by the pEH90-10am LE392 transformants revealed that both a fusion protein (approximately 160,000 daltons) and an unfused gD-1 related protein (approximately 38,000 daltons) were produced; both proteins immunoreact with rabbit anti-HSV-1 serum. The pEH90-10am LE392 transformants seem to produce both proteins in approximately equimolar amounts. The two proteins co-purify when isolated via a modification of the non-denaturing co-aggregate purification procedure described in Section 5.5 and in detail below.

The following mini-aggregate procedure was used to isolate host cell aggregates for screening analysis:

(1) Duplicate culture tubes containing 5 ml of fresh Luria broth containing 100μg/ml ampicillin were inoculated with 200μl of cells obtained from an overnight culture and grown for 90 minutes at 37° C. One of each duplicate was induced by the addition of lmM IPTG (final concentration). The inocula were then grown with shaking, for a further 5 hours at 37° C.

(2) The cells contained in a 3 ml aliquot of the culture were pelleted by centrifugation in a microcentrifuge (12,000 ×g) for 2 minutes. (N.B., the total volume of a microcentrifuge tube is 1.5 ml, therefore, a 1.5 ml aliquot was first pelleted and the supernatant was drawn off; another 1.5 ml aliquot was added to the same microcentrifuge tube and pelleted in the same tube.)

(3) The cell pellet was resuspended in 50 μl of 25% sucrose containing 50mM Tris-HCl, pH8, and the suspension was frozen by placing the tube in a dry ice/ethanol bath.

(4) The frozen suspension was thawed, 50 μl of 10mg/ml lysozyme in 0.25M Tris-HCl pH8 was added, and the suspension was incubated for 10 to 15 minutes on ice.

(5) After the 10 to 15 minute incubation 400μl of TET buffer (100mM Tris-HCl pH8, 50mM EDTA, 2% Triton X-100; TritonX-100 is a non-ionic detergent: polyoxyethylene (9-10) p-tert-octyl phenol) was added, the suspension was gently mixed and incubated for 5 minutes on ice. Then 500μl of 2×RIPA (2×RIPA is 20mM Tris-HCl, pH7.4, 300mM NaCl, 2% sodium deoxycholate, 2% NP-40, 0.2% SDS) was added and the suspension was mixed gently and incubated for 5 minutes on ice.

(6) The cells in the suspension were then sonicated for 10 seconds using a microprobe, and the suspension was cleared by centrifugation in a Sorvall SS34 rotor for 30 minutes at 10,000 r.p.m. (11,950 ×g).

(7) The supernatant was decanted and the pellet, which contains the co-aggregate proteins, was resuspended in 50 μl distilled H$_2$O to which 50μl of 2×Sample Buffer (2×Sample Buffer is composed of 10% SDS, 40mM Tris-HCl, ph6.8, 2% β-ME, and 0.02 volumes saturated solution of bromphenol blue) was added and mixed well. The mixture was boiled for 5 minutes and 25μl aliquots were applied to 10% SDS-polyacrylamide gels for electrophoresis.

After the proteins were separated by SDS-PAGE, they were transferred to nitrocellulose (i.e., a protein "blot" was done). The nitrocellulose was then treated with rabbit antisera directed against HSV-1 followed by $^{125}$I-labeled goat antiserum directed against rabbit immunoglobulin as a probe (Towbin, 1979, Proc. Natl. Acad. Sci. USA 76:4350). Autoradiograms of the protein blots clearly demonstrated that two bands immunoreacted with the anti-HSV-1 antibodies: a 160,000 dalton fusion protein (Cro/gD-1/β-galactosidase) and a 38,000 dalton gD-1 related protein (Cro/gD-1) or unfused gD protein (unfused to β-galactosidase). Thus, the unfused protein co-purifies with the fusion protein when the co-aggregate method of isolation is used for isolating proteins, and both the unfused gD (Cro/gD-1) and gD-fusion protein (Cro/gD-1/β-galactosidase) immunoreact with anti-HSV serum.

7. Deposit of Microorganisms

It is to be understood that all base pair sizes given for nucleotide sequences are approximate and are used for purposes of description. While the nucleotide sequences reported herein are believed to be accurate, any changes which do not significantly affect the processes or activity of the products described herein are intended to be included within the scope of the claimed invention. Furthermore, it is apparent that many modifications and variations of this invention as hereinbefore set forth may be made without departing from the spirit and scope thereof. The specific embodiments described are given by way of example only and the invention is limited only by the appended claims.

The following *E. coli* strains carrying the listed plasmids have been deposited with the Agricultural Research Culture Collection (NRRL), Peoria, Ill. and have been assigned the listed accession numbers:

| E. coli Strain | Plasmid | Accession Numbers |
| --- | --- | --- |
| (1) K-12, NF1829 | p141-2 | B-15665 |
| (2) K-12, NF1829 | p179-3 | B-15658 |
| (3) K-12, SK107 | p195-4 | B-15676 |
| (4) K-12, NF1829 | p214-1 | B-15656 |
| (5) K-12, NF1829 | p217-1 | B-15661 |
| (6) K-12, F'SK107 | p230-2/3 | B-15670 |
| (7) K-12, F'SK107 | p230-5/3 | B-15671 |
| (8) K-12, F'SK107 | p230-6/2 | B-15674 |
| (9) K-12, SK107 | p231-3 | B-15678 |
| (10) K-12, LE392 | pEH90-10am | B-15451 |

A culture of the deposited microorganisms will be made available to the public upon the grant of patent based upon the present application. It is to be understood that the availability of a deposit does not constitute a license to practice the subject invention in derogation of patent rights granted by the U.S. government. Furthermore, the present invention is not to be limited in scope by the microorganism deposited, since the deposited embodiment is intended as a single illustration of one aspect of the invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A process for stabilizing a foreign polypeptide produced in an *Escherichia coli* cell, comprising culturing an *Escherichia coli* cell capable of co-expressing at least one DNA sequence coding for a foreign polypeptide and at least one DNA sequence coding for an aggregate-forming polypeptide, wherein the DNA sequence coding for the aggregate-forming polypeptide is located on a recombinant vector, such that co-expression of the DNA coding for the foreign polypeptide and the DNA coding for the aggregate-forming polypeptide results in formation of an aggregate containing both the aggregate-forming polypeptide the foreign polypeptide and separating said aggregate from said cell.

2. The process according to claim 1, further comprising the steps of solubizing the aggregate and isolating the foreign polypeptied from the aggregate-forming polypeptide.

3. The process according to claim 1, wherein the DNA sequence coding for the foreign polypeptide is located on a recombinant vector, and the DNA sequence coding for the aggregate-forming polypeptide is located on a different recombinant vector.

4. The proecess according to claim 1, wherein the DNA sequence coding for the foreign polypeptide is located on a recombinant vector, and the DNA sequence coding for the aggregate-forming polypeptide is located on the same vector.

5. The process according to claim 4, wherein the DNA sequences coding for the foreign polypeptide and for the aggregate-forming polypeptide comprises a first DNA sequence coding for the foreign polypeptide connected in the correct translational reading frame to a second DNA sequence coding for a second polypeptide wherein a chain termination signal is located between said first and second DNA sequences in the correct translational reading frame, and the cell contains a chain terminator suppressor tRNA gene for such chain terminiation signal.

6. The process according to claim 5, wherein the chain termination signal has the sequence TAG.

7. The process according to claim 4, wherein the chain termination signal has the sequence TAA.

8. The process according to claim 5, wherein the chain termination signal has the sequence TGA.

9. The process according to claim 1, wherein the DNA sequence coding for the aggregate-forming polypeptide comprises a first DNA sequence coding for a polypeptide connected in the correct translational reading frame to a second DNA sequence coding for a second polypeptide.

10. The process according to claim 9, wherein the second DNA sequence codes for a major portion of a second polypeptide that is a native Escherichia coli polypeptide.

11. The process according to claim 9, wherein the second polypeptide is β-galactosidase.

12. The process according to claim 1, wherein the DNA sequence coding for the foreign polypeptide codes for a eucaryotic protein.

13. The process according to claim 1, wherein the DNA sequence coding for the foreign polypeptide codes for a procaryotic protein.

14. The process according to claim 1, wherein the DNA sequence coding for the foreign polypeptide codes for a viral protein.

* * * * *